United States Patent [19]
Cotting et al.

[11] Patent Number: 5,981,790
[45] Date of Patent: Nov. 9, 1999

[54] METHOD FOR PARTIALLY HYDROGENATING DINITRILES TO AMINONITRILES

[75] Inventors: Marie-Christine Cotting, Bron; Laurent Gilbert, Lyons; Philippe Leconte, Meyzieu, all of France

[73] Assignee: Rhone-Poulenc Fiber and Resin Intermediates, Courbevoie, France

[21] Appl. No.: 08/849,950

[22] PCT Filed: Dec. 12, 1995

[86] PCT No.: PCT/FR95/01643

§ 371 Date: Sep. 15, 1997

§ 102(e) Date: Sep. 15, 1997

[87] PCT Pub. No.: WO96/18603

PCT Pub. Date: Jun. 20, 1996

[30] Foreign Application Priority Data

Dec. 14, 1994 [FR] France .................................. 94 15282

[51] Int. Cl.⁶ .................................................. C07C 255/04
[52] U.S. Cl. ............................................................. 558/459
[58] Field of Search ................................................ 558/459

[56] References Cited

U.S. PATENT DOCUMENTS 4,248,799  2/1981  Drake .
4,362,671  12/1982  Diamond et al. .
5,151,543  9/1992  Ziemecki .

FOREIGN PATENT DOCUMENTS

93/12073  6/1993  WIPO .
93/16034  8/1993  WIPO .

*Primary Examiner*—Johann Richter
*Assistant Examiner*—Ebenezer Sackey
*Attorney, Agent, or Firm*—Burns, Doane, Swecker & Mathis, L.L.P.

[57] ABSTRACT

A process for the hemihydrogenation of aliphatic dinitriles to the corresponding aminonitriles using hydrogen in the presence of a catalyst, a strong inorganic base and water is disclosed. Using the disclosed process, a selectivity for the desired aminonitriles of at least 60% can be achieved.

25 Claims, No Drawings

METHOD FOR PARTIALLY HYDROGENATING DINITRILES TO AMINONITRILES

This appln. is a 371 of PCT/FR95/01643 filed on Dec. 12, 1995.

The present invention relates to the hemihydrogenation of dinitriles to corresponding aminonitriles.

The hydrogenation of dinitriles is generally carried out in order to prepare the corresponding diamines; thus, particularly, the hydrogenation of adiponitrile produces hexamethylenediamine, itself one of the two base compounds for the preparation of polyamide 6,6.

However, it may sometimes be found necessary to prepare not the diamine but the intermediate aminonitrile. This, for example, is the case—although no limitation is implied thereby—of the hemihydrogenation of adiponitrile to aminocapronitrile, a compound capable of being subsequently converted into caprolactam, a base compound for polyamide 6, or directly into polyamide 6.

Thus, U.S. Pat. No. 4,389,348 describes a process for hydrogenation of dinitrile to omega-aminonitrile, using hydrogen in an aprotic solvent medium and ammonia in the presence of rhodium deposited on a basic support.

U.S. Pat. No. 5,151,543 describes a process for partial hydrogenation of dinitriles to aminonitriles in a solvent in a molar excess of at least 2/1 in relation to the dinitrile, including liquid ammonia or an alkanol containing an inorganic base which is soluble in the said alkanol, in the presence of a catalyst of the Raney nickel or cobalt type.

WO-A-93/16034 describes a process for the preparation of 6-aminocapronitrile by the hydrogenation of adiponitrile, under pressure and at a temperature of 50 to 90° C., in the presence of an alkaline metal hydroxide or ammonium hydroxide, of a low valent transition metal complex and a Raney nickel catalyst. This process is carried out according to the examples in solvent such as a lower alkanol or a hydrocarbon.

The present invention deals with the preferential hydrogenation of a single nitrile functional group of a dinitrile (called hemihydrogenation in this text), so as to prepare the corresponding aminonitrile as a major product and the diamine only as a minor product.

More precisely, the invention relates to a process for the hemihydrogenation of aliphatic dinitriles to the corresponding aminonitriles, with the aid of hydrogen and in the presence of a catalyst chosen from Raney nickel, Raney cobalt, Raney nickel comprising a doping element chosen from the elements of groups IVb, VIb, VIIb and VIII of the Periodic Classification of the elements, as published in the *Handbook of Chemistry and Physics* (Weast, 5th edition of 1970–1971) and zinc and Raney cobalt comprising a doping element chosen from the elements of groups IVb, VIb, VIIb and VIII of the Periodic Classification of the elements and zinc, and of a strong inorganic base derived from an alkali or alkaline-earth metal, characterized in that:

the initial hydrogenation mixture comprises water in a proportion of at least 0.5% by weight relative to the totality of the liquid compounds of the said mixture, the diamine and/or the aminonitrile which are liable to be formed from the dinitrile to be hydrogenated and the unconverted dinitrile in a proportion of 80% to 99.5% for the combined total of these three compounds relative to the totality of the liquid compounds of the said mixture, the degree of conversion of the dinitrile can reach 95%, and in that the said process makes it possible to obtain a selectivity for the aminonitriles being aimed at of at least 60%.

The degree of conversion of the dinitrile is preferably at least 70%.

The aliphatic dinitriles which may be used in the process of the invention are more particularly the dinitriles of general formula (I):

$$NC—R—CN \quad (I)$$

in which R denotes a linear or branched alkylene or alkenylene group containing from 1 to 12 carbon atoms.

Dinitriles of formula (I) in which R denotes a linear or branched alkylene radical containing from 1 to 6 carbon atoms are preferably used in the process of the invention.

Examples of such dinitriles which may be mentioned are especially adiponitrile, methylglutaronitrile, ethylsuccinonitrile malononitrile, succinonitrile and glutaronitrile and mixtures thereof, especially the mixtures of adiponitrile and/or methylglutaronitrile and/or ethylsuccinonitrile that are liable to originate from the same process for the synthesis of adiponitrile.

In practice, the case where $R=(CH_2)_4$ will be the most frequent one, because this corresponds to the use of adiponitrile (ADN) in the present process.

The strong inorganic base generally consists of alkali metal or alkaline-earth metal hydroxides, carbonates and alkanolates. It is preferably chosen from alkali metal hydroxides, carbonates and alkanolates.

As a matter of priority, the strong inorganic base used is chosen from the following compounds: LiOH, NaOH, KOH, RbOH, CsOH and mixtures thereof.

NaOH and KOH are employed most frequently in practice as a good performance-price compromise, although RbOH and CsOH can give very good results.

The reaction mixture has a composition which varies depending on the type of implementation of the process.

In fact, if the process is carried out noncontinuously, as is the case especially in the laboratory embodiments or small intermittent manufacture, the initial reaction mixture will become gradually enriched in aminonitrile and, in a lesser proportion, in diamine, while the dinitrile concentration will be capable either of decreasing if all or most of the said dinitrile is charged at the very beginning of the hemihydrogenation, or of remaining relatively constant if the dinitrile is introduced gradually during the reaction.

On the other hand, if the process is conducted continuously, the average composition of the reaction mixture reaches values that are determined by the selectivities of the reaction.

Water is generally present in a quantity which is smaller than or equal to 20%. The water content of the reaction mixture is preferably between 2% and 15% by weight relative to the combined total of the liquid constituents of the said mixture.

The concentration of the aminonitrile aimed at and/or of the corresponding diamine and of the unconverted dinitrile in the reaction mixture is generally between 85% and 98% by weight relative to the combined total of the liquids included in the said reaction mixture.

In continuous operation of the process of the invention the average concentration will be determined by the ratio of the respective selectivities for aminonitrile and for diamine and by the rate of introduction of the dinitrile.

The quantity of strong inorganic base is advantageously greater than or equal to 0.1 mol/kg of catalyst. It is preferably between 0.1 mol and 3 mol per kg of catalyst and still more preferably between 0.2 and 2 mol/kg of catalyst.

To obtain an optimum selectivity for aminonitrile the strong inorganic base/catalyst ratio may be modified according to the base used. Thus, with KOH, RbOH and CsOH, this ratio will be still more preferably from 0.2 to 1.0 mol per kg of catalyst, particularly of Raney nickel, whether doped or not. With NaOH and LiOH, this ratio will be still more preferably from 0.2 to 1.5 mol per kg of catalyst, particularly of Raney nickel, whether doped or not.

The catalyst employed in the process may be a Raney nickel, a Raney cobalt, a Raney nickel or a Raney cobalt comprising, besides the nickel or the cobalt and the residual quantities of the metal removed from the original alloy during the preparation of the catalyst, that is to say generally aluminum, one or several other elements, often called dopants, such as, for example, chromium, titanium, molybdenum, tungsten, iron or zinc. Among these doping elements, chromium, titanium and their mixtures with each other and their mixtures with iron are considered to be the most advantageous ones. These dopants usually represent from 0% to 10% and preferably from 0% to 5% by weight per weight of nickel or of cobalt.

When the catalyst contains a dopant such as chromium or titanium, it is also advantageous to take the strong base/dopant ratio into account. Thus, a KOH/dopant ratio of 12 to 30 mol per kg of dopant and an NaOH/dopant ratio of 12 to 50 mol per kg of dopant are preferably used.

The quantity of catalyst which is used may vary very widely as a function especially of the method of operation which is adopted or of the reaction conditions which are chosen. Thus, if the dinitrile is introduced gradually into the reaction mixture, the weight ratio of catalyst/dinitrile to be hydrogenated will be much higher than if all the dinitrile is used at the very beginning of the reaction. To give an indication, from 0.5% to 50% by weight of catalyst may be employed relative to the total weight of the reaction mixture, and in most cases from 1% to 35%.

With a given catalyst and with a given degree of conversion of the dinitrile, the yield of aminonitrile passes through a maximum that is determined by the base/Ni or base/Co ratio chosen in the ranges of values indicated above.

At a constant degree of conversion of the dinitrile, the optimum yield of aminonitrile also depends on the nature and on the content of dopant, on the quantity of water in the reaction mixture and on the temperature.

The overall selectivity for aminonitrile is improved by the increase in the value of the rate constant of hydrogenation of the dinitrile to aminonitrile and not by the decrease in the value of the rate constant of hydrogenation of the aminonitrile to diamine. It is essentially the rate constant of the first of the two consecutive reactions that is affected by the various parameters indicated above.

The process of the invention is generally carried out at a reaction temperature which is lower than or equal to 150° C., preferably lower than or equal to 120° C. and, still more preferably, lower than or equal to 100° C.

In concrete terms, this temperature is between the ambient temperature (approximately 20° C.) and 100° C.

Before, simultaneously with or after the heating, the reaction vessel is brought to the appropriate hydrogen pressure, that is to say, in practice, of between 1 bar (0.10 MPa) and 100 bar (10 MPa) and preferably between 5 bar (0.5 MPa) and 50 bar (5 MPa).

The reaction period can vary as a function of the reaction conditions and of the catalyst.

In noncontinuous operation it may vary from a few minutes to several hours.

In continuous operation, which is the preferable industrial method for the process according to the invention, the duration is obviously not a tangible parameter.

It should be noted that, according to the operating conditions, a person skilled in the art may modify the chronology of the stages of the process according to the invention.

The other conditions which control the hydrogenation (using a continuous or noncontinuous method) in accordance with the invention, are related to technical arrangements which are conventional and known per se.

The examples which follow illustrate the invention.

The following abbreviations may be employed in these examples:

```
ADN = adiponitrile
ACN = aminocapronitrile
HMD = hexamethylenediamine
DC = degree of conversion
CY = selectivity based on the initial
     substrate converted (based on ADN
     in this case).
```

EXAMPLE 1

Into a 300-ml stainless steel reactor fitted with stirring of the Rushtone Cavitator type, means for introducing reactants and hydrogen and a temperature control system, are charged:

| | |
|---|---|
| adiponitrile | 95.1 g |
| hexamethylenediamine | 94.2 g |
| water | 21.1 g |
| KOH | 0.056 g |
| Raney Ni (containing 1.7% of Cr) | 2.5 g of Ni |

In this example there is 0.4 mol KOH/kg Raney Ni.

The reaction mixture is heated to 50° C. after the reactor has been purged with nitrogen and then with hydrogen; the pressure is then adjusted to 2 MPa at this temperature by continuous addition of hydrogen. The progress of the reaction is followed by using the consumption of hydrogen and analysis by vapour phase chromatography (GC) of a sample of the reaction mixture. When the optimum yield is reached, the reaction is stopped by stopping the stirring and cooling of the reaction mixture.

The following results are obtained:

| | |
|---|---|
| reaction time: | 80 min |
| DC of ADN: | 83.5% |
| CY of ACN: | 77.5% |

EXAMPLE 2

Example 1 is repeated in the same operating conditions and with the following charges:

| | |
|---|---|
| adiponitrile | 95.1 g |
| hexamethylenediamine | 95.4 g |
| water | 21.1 g |
| KOH | 0.113 g |
| Raney Ni (containing 1.7% of Cr) | 2.5 g of Ni |

In this example there is 0.8 mol KOH/kg Raney Ni.
The following results are obtained:
reaction time: 80 min
DC of ADN: 81.9%
CY of ACN: 68.3%

EXAMPLE 3

Example 1 is repeated in the same operating conditions and with the following charges:

| | |
|---|---|
| adiponitrile | 27.4 g |
| hexamethylenediamine | 166.4 g |
| water | 19.4 g |
| KOH | 0.115 g |
| Raney Ni (containing 1.7% of Cr) | 2.5 g of Ni |

In this example there is 0.8 mol KOH/kg Raney Ni.
The following results are obtained:
reaction time: 20 min
DC of ADN: 71.2%
CY of ACN: 77.0%

EXAMPLE 4

Example 1 is repeated in the same operating conditions and with the following charges:

| | |
|---|---|
| adiponitrile | 142.4 g |
| hexamethylenediamine | 47.75 g |
| water | 21.1 g |
| KOH | 0.053 g |
| Raney Ni (containing 1.7% of Cr) | 2.5 g of Ni |

In this example there is 0.4 mol KOH/kg Raney Ni.
The following results are obtained:
reaction time: 103 min
DC of ADN: 76.2%
CY of ACN: 77.2%

EXAMPLE 5

Example 1 is repeated in the same operating conditions and with the following charges:

| | |
|---|---|
| adiponitrile | 95.1 g |
| hexamethylenediamine | 97.1 g |
| water | 21.1 g |
| KOH | 0.056 g |
| Raney Ni (containing 2.4% of Cr and 1.3% of Fe) | 2.5 g of Ni |

In this example there is 0.4 mol KOH/kg Raney Ni and 16.7 mol KOH/kg Cr.
The following results are obtained:
reaction time: 45 min
DC of ADN: 82.4%
CY of ACN: 74.3%

EXAMPLE 6

Example 1 is repeated in the same operating conditions and with the following charges:

| | |
|---|---|
| adiponitrile | 95.0 g |
| hexamethylenediamine | 97.3 g |
| water | 21.1 g |
| KOH | 0.056 g |
| Raney Ni (containing 3.0% of Cr and 1.6% of Fe) | 2.5 g of Ni |

In this example there is 0.4 mol KOH/kg Raney Ni and 13.3 mol KOH/kg Cr.

The following results are obtained:
reaction time: 85 min
DC of ADN: 84.5%
CY of ACN: 65.9%

EXAMPLE 7

Into a 150-ml stainless steel reactor fitted with magnetic stirring, means for introducing reactants and hydrogen and a temperature control system, are charged:

| | |
|---|---|
| adiponitrile | 21.65 g |
| hexamethylenediamine | 21.65 g |
| water | 4.75 g |
| NaOH | 0.0372 g |
| Raney Ni (containing 1.7% of Cr) | 0.58 g of Ni |

In this example there is 1.6 mol NaOH/kg Raney Ni.

The reaction mixture is heated to 50° C. after the reactor has been purged with nitrogen and then with hydrogen; the pressure is then adjusted to 2 MPa at this temperature by continuous addition of hydrogen. The progress of the reaction is followed by using the consumption of hydrogen and analysis by vapour phase chromatography (GC) of a sample of the reaction mixture. When the optimum yield is reached, the reaction is stopped by stopping the stirring and cooling of the reaction mixture.

The following results are obtained:
reaction time: 90 min
DC of ADN: 70%
CY of ACN: 62%

EXAMPLE 8

Example 7 is repeated in the same operating conditions with the following charges:

| | |
|---|---|
| adiponitrile | 21.6 g |
| hexamethylenediamine | 21.8 g |
| water | 4.75 g |
| NaOH | 0.0046 g |
| Raney Ni (containing 1.7% of Cr) | 0.58 g of Ni |

In this example there is 0.2 mol NaOH/kg Raney Ni.
The following results are obtained:
reaction time: 107 min
DC of ADN: 76%
CY of ACN: 62%

EXAMPLE 9

Example 7 is repeated in the same operating conditions with the following charges:

| | |
|---|---|
| adiponitrile | 21.6 g |
| hexamethylenediamine | 21.7 g |
| water | 4.78 g |
| NaOH | 0.0094 g |
| Raney Ni (containing 1.7% of Cr) | 0.58 g of Ni |

In this example there is 0.4 mol NaOH/kg Raney Ni.
The following results are obtained:
reaction time: 67 min
DC of ADN: 80%
CY of ACN: 69%

EXAMPLE 10

Example 7 is repeated in the same operating conditions with the following charges:

| | |
|---|---|
| adiponitrile | 21.6 g |
| hexamethylenediamine | 21.6 g |
| water | 4.75 g |
| NaOH | 0.0187 g |
| Raney Ni (containing 1.7% of Cr) | 0.58 g of Ni |

In this example there i s 0.8 mol NaOH/kg Raney Ni.
The following results are obtained:
reaction time: 69 min
DC of ADN: 75%
CY of ACN: 73%

EXAMPLE 11

Example 7 is repeated in the same operating conditions with the following charges:

| | |
|---|---|
| adiponitrile | 21.65 g |
| hexamethylenediamine | 21.65 g |
| water | 4.75 g |
| KOH | 0.026 g |
| Raney Ni (containing 3.6% of Cr) | 0.58 g of Ni |

In this example there is 0.8 mol KOH/kg Raney Ni.
The following results are obtained:
reaction time: 51 min
DC of ADN: 75%
CY of ACN: 67%

EXAMPLE 12

Into a metallic reator fitted with stirring of the Cavitator type, means for introducing reactants and hydrogen and different control systems, are charged:

| | |
|---|---|
| adiponitrile | 2856 kg |
| hexamethylenediamine | 1151 kg |
| water | 588 kg |
| KOH | 0.83 kg |
| Raney Ni (containing 1.7% of Cr) | 37 kg |

The run is carried out in the operating conditions described in example 1.
The following results are obtained:

| | |
|---|---|
| reaction time: | 3 hr 30 min |
| DC of ADN: | 86% |
| CY of ACN | 64% |

EXAMPLE 13

Into a 150-ml stainless steel reator fitted with magnetic stirring, means for introducing reactants and hydrogen and a temperature control system, are charged:

| | |
|---|---|
| adiponitrile | 6 g |
| hexamethylenediamine | 41.16 g |
| water | 0.84 g |
| CsOH | 0.054 g |
| Raney Ni (containing 12% of Fe) | 0.4 g |

In this example there is 0.9 mol CsOH/kg Raney Ni

The reaction mixture is heated to 80° C. after the reactor has been purged with nitrogen and then with hydrogen; the pressure is then adjusted to 2.5 MPa at this temperature by continuous addition of hydrogen. The progress of the reaction is followed by using the consumption of hydrogen and analysis by vapour phase chromatography (GC) of a sample of the reaction mixture. When the optimum yield is reached, the reaction is stopped by stopping the stirring and cooling of the reaction mixture.

The following results are obtained:

| | |
|---|---|
| reaction time: | 50 min |
| DC of ADN: | 89% |
| CY of ACN | 65% |

EXAMPLE 14

Example 13 is repeated in the same operating conditions with the following charges:

| | |
|---|---|
| adiponitrile | 6 g |
| hexamethylenediamine | 37.8 g |
| water | 4.2 g |
| CsOH | 0.036 g |
| Raney Ni (containing 1.5% of Ti) | 0.4 g |

In this example there is 0.6 mol CsOH/kg Raney Ni.
The following results are obtained:

| | |
|---|---|
| reaction time: | 20 min |
| DC of ADN: | 90% |
| CY of ACN | 60% |

We claim:

1. Process for the hemihydrogenation of dinitriles to the corresponding aminonitriles, with the aid of hydrogen and in the presence of a catalyst chosen from Raney nickel, Raney cobalt, Raney nickel comprising a doping element chosen from the elements of groups IVb, VIb, VIIb, and VIII of the Periodic Classification of the elements and zinc and Raney cobalt comprising a doping element chosen from the elements of groups IVb, VIb, VIIb, and VIII of the Periodic Classification of the elements and zinc, and of a strong inorganic base derived from an alkali or alkaline-earth metal, wherein:

the initial hydrogenation mixture comprises water in a proportion of between 2.0% by weight and 15.0% by weight relative to the totality of the liquid compounds of the said mixture, the diamine and/or the aminonitrile which are liable to be formed from the dinitrile to be hydrogenated and the unconverted dinitrile in a proportion of 80% to 99.5% for the combined total of these three compounds relative to the totality of the liquid compounds of the said mixture, the degree of conversion of the dinitrile can reach 95% and in that the said process makes it possible to obtain a selectivity for the aminonitriles being aimed at of at least 60%.

2. Process according to claim 1, wherein the degree of conversion of the dinitrile is at least 70%.

3. Process according to claim 1, wherein the inorganic base comprises alkali metal or alkaline-earth metal hydroxides, carbonates or alkanolates.

4. Process according to claim 1, wherein the strong inorganic base comprises LiOH, NaOH, KOH, RbOH, CsOH or mixtures thereof.

5. Process according to claim 1, wherein the quantity of inorganic base which is present in the reaction mixture is greater than or equal to 0.1 mole per kilogram of catalyst.

6. Process according to claim 1, wherein the quantity of KOH, RbOH or CsOH inorganic base present in the reaction mixture is from 0.2 to 1.0 mol per kg of catalyst, whether doped or not.

7. Process according to claim 1, wherein the quantity of NaOH or LiOH inorganic base present in the reaction mixture is from 0.2 to 1.5 mol per kg of catalyst, whether doped or not.

8. Process according to claim 1, wherein the aliphatic dinitriles which may be used in the process of the invention are the dinitriles of general formula (I):

NC—R—CN            (I)

in which R denotes a linear or branched alkylene or alkenylene group containing from 1 to 12 carbon atoms.

9. Process according to claim 1, wherein the concentration of the aminonitrile aimed at and/or of the corresponding diamine and of the unconverted dinitrile in the reaction mixture is between 85% and 98% by weight relative to the combined total of the liquids included in said reaction mixture.

10. Process according to claim 1, wherein the catalyst employed is a Raney nickel, a Raney cobalt, a Raney nickel or a Raney cobalt comprising one or several other doping elements chromium, titanium, molybdenum, tungsten, iron or zinc.

11. Process according to claim 1, wherein the catalyst employed is a Raney nickel comprising at least one doping element comprising chromium, titanium, or their mixtures with each other or their mixtures with iron.

12. Process according to claim 1, wherein the catalyst employed is a Raney nickel comprising from 0% to 10 of at least one doping element by weight per weight of nickel.

13. Process according to claim 1, wherein the catalyst contains a dopant comprising chromium or titanium and that a KOH/dopant ratio of 12 to 30 mol per kg of dopant or an NaOH/dopant ratio of 12 to 50 mol per kg of dopant is used.

14. Process according to claim 1, wherein the catalyst represents from 0.5% to 50% by weight relative to the total weight of the reaction mixture.

15. Process according to claim 1, which is carried out at a reaction temperature which is lower than or equal to 150° C.

16. Process according to claim 1, wherein the operation is carried out at a hydrogen pressure of between 1 bar (0.10 MPa) and 100 bar (10 MPa).

17. Process according to claim 3, wherein the inorganic base comprises alkali metal hydroxide, carbonates and alkanolates.

18. Process according to claim 5, wherein the quantity of inorganic base is between 0.1 and 3 moles per kilogram of catalyst.

19. Process according to claim 6, wherein the catalyst is Raney nickel.

20. Process according to claim 7, wherein the catalyst is Raney nickel.

21. Process according to claim 8, wherein R denotes a linear or branched alkylene radical containing from 1 to 6 carbon atoms.

22. Process according to claim 12, wherein said Raney nickel comprises from 0% to 5% of at least one doping element.

23. Process according to claim 14, wherein said catalyst represents from 1% to 35% by weight.

24. Process according to claim 15, which is carried out at a reaction temperature which is lower than or equal to 120° C.

25. Process according to claim 16, wherein the pressure is between 5 bar (0.5 MPa) and 50 bar (5 Mpa).

* * * * *